US008885160B2

(12) United States Patent
Rabus et al.

(10) Patent No.: US 8,885,160 B2
(45) Date of Patent: Nov. 11, 2014

(54) MICROSPECTROMETER

(75) Inventors: Dominik Rabus, Forchtenberg (DE);
Michael Winkler, Weissbach (DE);
Christian Oberndorfer, Schwaebisch Hall (DE)

(73) Assignee: Buerkert Werke GmbH, Ingelfingen (DE)

( * ) Notice: Subject to any disclaimer, the term of this patent is extended or adjusted under 35 U.S.C. 154(b) by 509 days.

(21) Appl. No.: 12/866,078

(22) PCT Filed: Feb. 25, 2009

(86) PCT No.: PCT/EP2009/001339
§ 371 (c)(1),
(2), (4) Date: Dec. 16, 2010

(87) PCT Pub. No.: WO2009/106313
PCT Pub. Date: Sep. 3, 2009

(65) Prior Publication Data
US 2011/0080583 A1    Apr. 7, 2011

(30) Foreign Application Priority Data

Feb. 26, 2008 (DE) .................... 20 2008 002 683 U
Mar. 20, 2008 (DE) .................... 20 2008 003 977 U

(51) Int. Cl.
| G01J 3/00 | (2006.01) |
| G01J 3/28 | (2006.01) |
| G01J 3/02 | (2006.01) |
| G01N 21/25 | (2006.01) |
| G01J 3/04 | (2006.01) |
| G01N 21/53 | (2006.01) |

(52) U.S. Cl.
CPC ...... *G01N 21/255* (2013.01); *G01N 2201/0628* (2013.01); *G01J 3/02* (2013.01); *G01J 3/021* (2013.01); *G01J 3/0259* (2013.01); *G01J 3/04* (2013.01); *G01J 3/0291* (2013.01); *G01J 3/0237* (2013.01); *G01J 3/0256* (2013.01); *G01N 21/532* (2013.01)
USPC .......................... 356/328; 356/300; 356/326

(58) Field of Classification Search
USPC ............................... 356/300, 326, 328, 72–73
See application file for complete search history.

(56) References Cited

U.S. PATENT DOCUMENTS 4,886,341 A * 12/1989 Oishi et al. .................... 359/575
5,424,826 A *  6/1995 Kinney ......................... 356/326

(Continued)

FOREIGN PATENT DOCUMENTS

| DE | 26 00 371 A1 | 7/1976 |
| DE | 41 22 925 A1 | 1/1993 |

(Continued)

OTHER PUBLICATIONS

Machine-translation of DE 10 2006 035 581 (Gindele et al.).*

(Continued)

*Primary Examiner* — Tarifur Chowdhury
*Assistant Examiner* — Hina F Ayub
(74) *Attorney, Agent, or Firm* — Tarolli, Sundheim, Covell & Tummino LLP

(57) ABSTRACT

The compact microspectrometer for fluid media has, in a fixed spatial coordination in a housing, a light source, a fluid channel, a reflective diffraction grating, and a detector. The optical measuring path starting from the light source passes through the fluid channel and impinges on the diffraction grating. The spectral light components reflected by the diffraction grating impinge on the detector.

17 Claims, 4 Drawing Sheets

(56) References Cited

U.S. PATENT DOCUMENTS

| | | | |
|---|---|---|---|
| 5,856,870 | A | 1/1999 | Curtiss |
| 6,075,252 | A | 6/2000 | Atkinson et al. |
| 2003/0098975 | A1 | 5/2003 | Mori et al. |
| 2004/0179194 | A1* | 9/2004 | Schmilovitch et al. ....... 356/244 |
| 2005/0030533 | A1* | 2/2005 | Treado ........................ 356/326 |
| 2005/0151966 | A1* | 7/2005 | Packirisamy et al. ......... 356/328 |
| 2007/0164221 | A1 | 7/2007 | Russell |
| 2007/0211250 | A1* | 9/2007 | Teichmann et al. ........... 356/328 |

FOREIGN PATENT DOCUMENTS

| | | |
|---|---|---|
| DE | 44 34 814 A1 | 4/1996 |
| DE | 197 17 014 A1 | 10/1998 |
| DE | 103 05 093 A1 | 8/2004 |
| DE | 103 60 563 A1 | 7/2005 |
| DE | 10 2004 030 029 B3 | 12/2005 |
| DE | 10 2006 035 581 B3 | 2/2008 |
| JP | 51094287 | 8/1976 |
| JP | 52119376 | 10/1977 |
| JP | 61107121 | 5/1986 |
| JP | 1308943 | 12/1989 |
| JP | 3010126 | 1/1991 |
| JP | 4223235 | 8/1992 |
| JP | 8114501 | 5/1996 |
| JP | 11241948 | 9/1999 |
| JP | 2000161654 | 6/2000 |
| JP | 2003518241 | 6/2003 |
| JP | 2003279483 | 10/2003 |
| JP | 2007263983 | 10/2007 |
| WO | WO-2004/070369 A1 | 8/2004 |
| WO | WO-2007/050123 A2 | 5/2007 |

OTHER PUBLICATIONS

Machine translation of DC 26 00 371 (Beetz et al.).*

* cited by examiner

MICROSPECTROMETER

FIELD OF THE INVENTION

The present invention relates to a microspectrometer.

BACKGROUND OF THE INVENTION

Microspectrometers are known. Components such as a diffraction grating, a mirror, evaluation electronics, and optical fibers are typically arranged in a housing or on a base plate, these components coupling the light to be analyzed into the spectrometer. A light source and the sample to be analyzed, through which the light of the external light source radiates, are provided outside of the microspectrometer. The light dispersed into its spectral components by the diffraction grating reaches a plurality of photodetectors via optical fibers.

SUMMARY OF THE INVENTION

The invention provides a microspectrometer which can be configured to be extremely compact and without any external components and only has a fluidic interface and electrical connections to the outside.

One of the advantages of the invention indicated in the appended claims is that it allows the continuous spectroscopy of an analyte, which is of major importance for monitoring the quality of drinking water, for example.

In addition, possible sources of error are excluded because the light source need not be newly aligned in each measurement with the container containing the analyte to be measured.

Any additional lenses that are required in known microspectrometers to couple light into the optical fiber, and also the optical fiber itself are dispensable. The light dispersed into its spectral components by the diffraction grating can be directly received by a photodetector row without any detours via optical fibers. In an alternative embodiment, the diffraction grating is mounted for rotary motion, so that one single photodetector may be used instead of a detector row.

It is particularly favorable for the housing of the microspectrometer to be manufactured as a rigid molded body from an at least partly transparent plastic material in an injection molding procedure. The fluid channel is then guided transversely through a solid region of the molded body from one side face to the opposite face. In an advantageous embodiment, the diffraction grating required is molded into a face of the molded body during injection molding.

But it is also possible to insert a grating into a recess of the housing after the injection molding process.

For reflective surfaces that are intended to act as mirrors, metal layers may subsequently be vapor deposited, or a suitable film is injection molded as a backing.

The light source may be an LED, for example, and be integrated into the molded body as an insert. But the light source could also be inserted into a recess of the plastic part and be subsequently fastened by bonding, for example.

It is also possible to use OLED or other known methods such as laser technology for generating the light source.

When a plurality of different light sources is integrated into a microspectrometer, one device can be used to advantage to carry out a plurality of spectral measurements of different wavelengths.

A further light source could be arranged below or above the fluid channel, for example. The scattered light would then be radiated at an angle of 90° on the same path as the measuring path described. The scattered light impinges on the grating, is spectrally dispersed and reaches the electronic evaluation unit.

According to one variant, or additionally, a separate light source radiates transversely through the fluid channel and the scattered light occurring in the process is captured directly (without a spectral dispersion) by means of a further photodiode. The scattered light intensity is measured and evaluated separately.

BRIEF DESCRIPTION OF THE DRAWINGS

Advantageous embodiments will now be described in more detail with reference to the accompanying drawings, in which.

DESCRIPTION OF PREFERRED EMBODIMENTS

Figure 1:
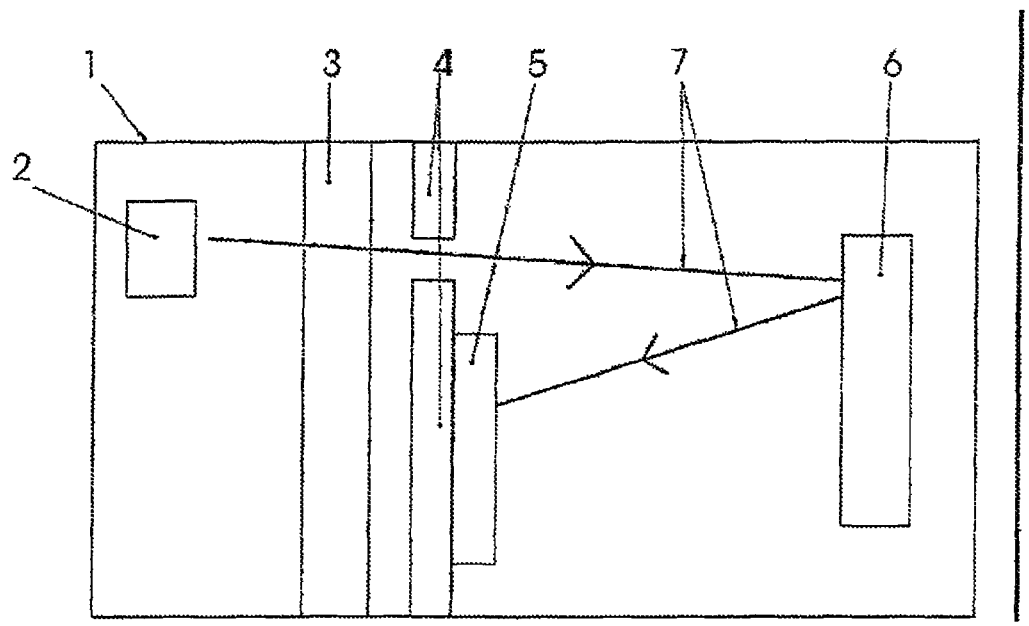
FIG. 1 shows a top view of an exemplary embodiment of the microspectrometer in a schematic illustration, with the housing open.

In the embodiment of a microspectrometer according to the invention as shown in FIG. 1, a light source 2 and a diffraction grating 6 are arranged on opposite sides in a housing 1.

A fluid channel 3 extends through the housing 1. The channel 3 may either be filled with a medium to be analyzed and be closed, or this medium may flow through the channel continuously. For this purpose, the fluid channel 3 can be connected to conduits (not illustrated in FIG. 1) for conveying the medium to and away from the spectrometer. The fluid channel 3 is arranged in the housing such that it is positioned on the optical measuring path between the light source 2 and the grating 6.

The fluid channel 3 must be manufactured from a light-transmissive material. The fluid channel 3 may either be provided already completely or partly in the injection mold for the housing 1 of the microspectrometer, or the channel or window-like parts thereof made from a transparent material such as glass or PMMA are subsequently inserted into the housing.

To filter out any undesirable scattered light, a diaphragm 4 is provided between the fluid channel 3 and the grating 6 and has an opening that is positioned such that light from the light source 2 impinges on the grating 6.

Ideally, the diameter of the diaphragm 4 is adjustable.

A mirror 5 is arranged between the diaphragm 4 and the grating 6 such that light reflected by the grating 6 impinges on the mirror. The mirror 5 may be part of the diaphragm 4, for example, arranged so as to face the grating 6, rather than the light source 2.

The mirror 5 directs incident light on to an evaluation unit (not illustrated in FIG. 1). This evaluation unit may be a photodetector, for example, such as an organic photodiode array.

In addition to the individual components required for the spectrometer, FIG. 1 shows the beam path 7 of the optical measuring path. Ideally, light from the light source 2 passes through the fluid channel 3 at an angle of incidence of 90°, passes through the diaphragm 4, and reaches the grating 6, which spectrally disperses the light and reflects it onto the mirror 5, which deflects the light to the evaluation unit.

The evaluation unit may be arranged inside the microspectrometer or else be positioned outside.

Figure 2:
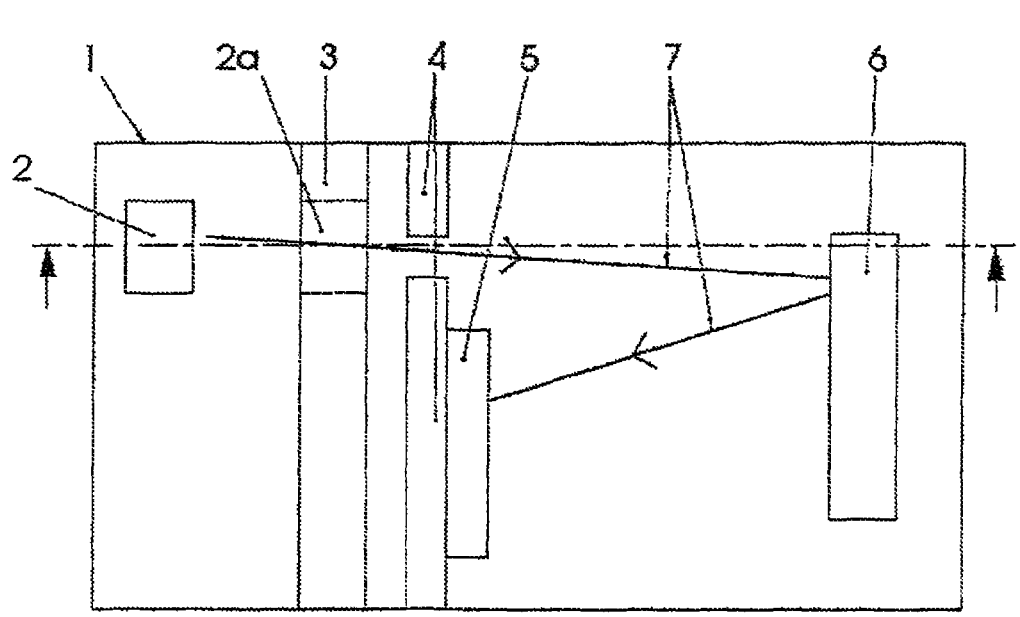
FIG. 2 shows a top view of a second exemplary embodiment of the microspectrometer in a schematic illustration, with the housing open.
Figure 3:
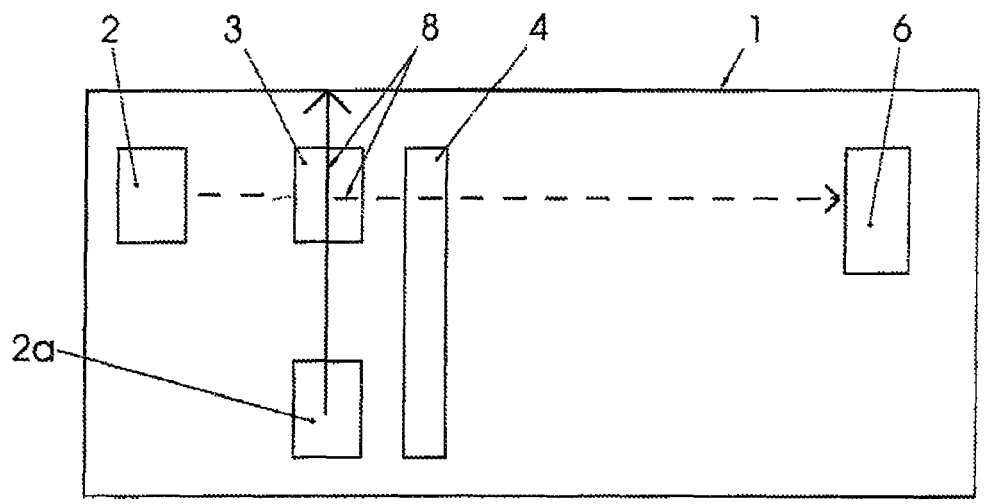
FIG. 3 shows a section of FIG. 2.

As shown in FIG. 2 and FIG. 3, in a second exemplary embodiment a second light source 2a, e.g. an LED, is arranged below the fluid channel, which likewise emits light transversely through the fluid channel. Stray light scattered off the main beam at an angle of 90° (broken line) passes, as per the beam path 8, through the diaphragm 4 and reaches the diffraction grating 6 and the evaluation unit, e.g. for the purpose of turbidity measurement. Here, the light source 2 is not activated simultaneously with the light source 2a. When the two light sources 2 and 2a are activated alternately, it is therefore possible to determine, using the same device, the turbidity and the concentration of constituents in liquids one after the other.

In this embodiment, the evaluation of the scattered light is effected with a spectral dispersion by the diffraction grating 6.

Figure 4:
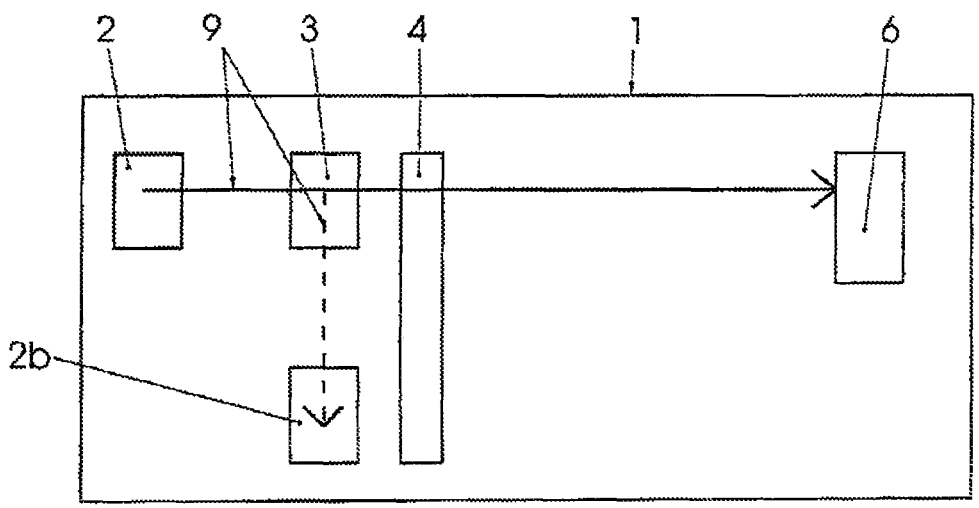
FIG. 4 shows a sectional drawing of a further exemplary embodiment.

FIG. 4 shows the sectional drawing of a further exemplary embodiment in which the evaluation of the scattered light is effected without spectral dispersion.

The arrangement of the individual components is identical with that of the first exemplary embodiment, except that a photodiode 2b is additionally provided below the fluid channel 3.

The photodiode 2b detects scattered light that is radiated at an angle of 90° from the main beam which is emitted by the light source 2 and which radiates transversely through the fluid channel 3. The beam path of the scattered light is illustrated by the arrow 9 in a broken line.

In this exemplary embodiment, the main beam of the light source 2 can be optically dispersed by means of the grating and evaluated and the scattered light occurring in the process can at the same time be captured directly with the aid of the photodiode 2b and the scattered light intensity be measured.

Figure 5:
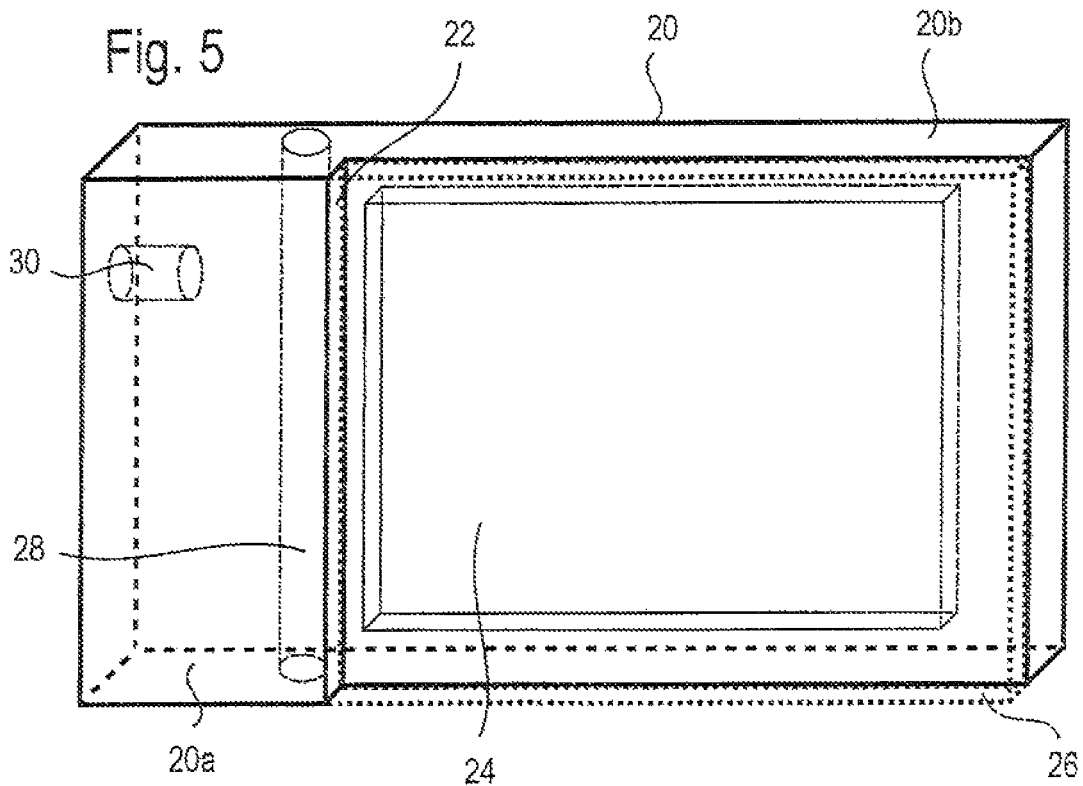
FIG. 5 shows a rigid molded body that is suitable for use as a housing.

The rigid molded body 20 that is shown in FIG. 5 and is suitable as a housing of the microspectrometer is a flat cuboid having a solid block 20a which continues into a flat region 20b by means of a step 22, a rectangular recess 24 being formed in the region 20b. This recess 24 can be closed by a cover 26 which adjoins the block 20a so as to be flush therewith. The molded body 20 is produced by injection molding of a plastic material, in particular a transparent plastic material such as polymethylacrylate. The block 20a has a duct 28 recessed therein which, starting from a side face, is guided up to the opposite side face. Furthermore, a cylindrical recess 30 is incorporated in the block 20a perpendicularly to the duct 28.

Figure 6:
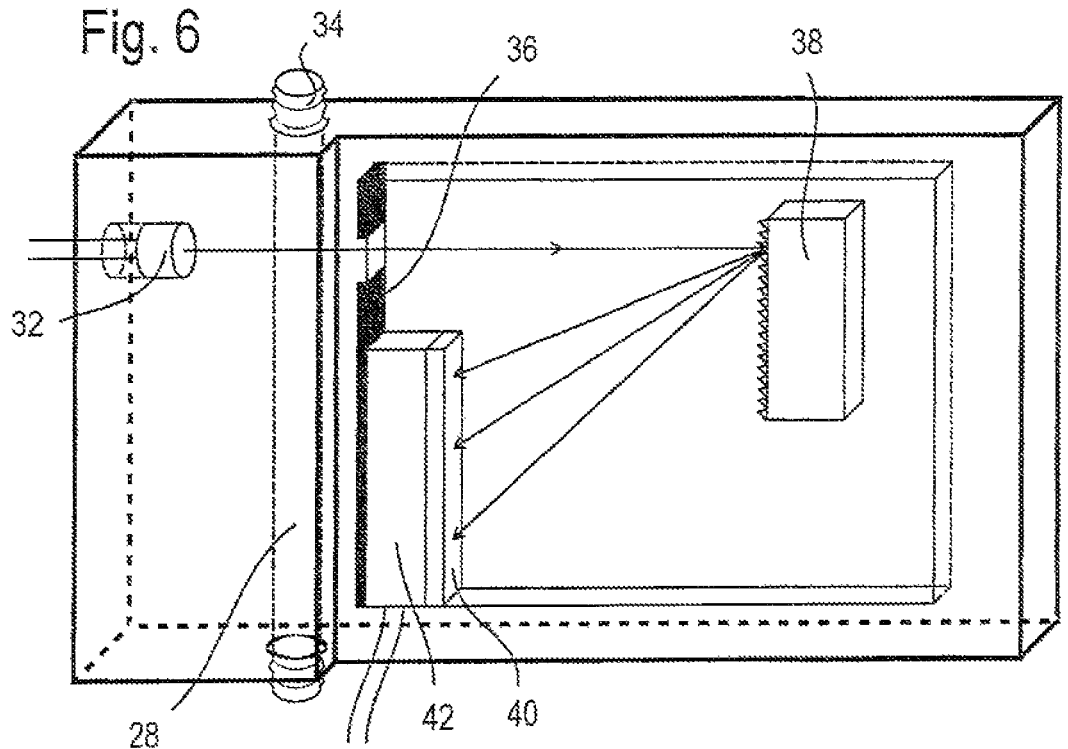
FIG. 6 shows an embodiment using the housing according to FIG. 5.

As shown in FIG. 6, a light source such as an LED 32 is introduced into the recess 30. The duct 28 is provided with fluidic connecting pieces 34 at its ends. The recess 24 accommodates all further components of the microspectrometer: the diaphragm 36, the diffraction grating 38, and the photodetector row 40 with the electronic evaluation unit 42. Further optical and/or electronic components may, of course, be arranged in the recess 24. Also, a plurality of light sources for different spectral regions may be arranged in the block 20a.

To the outside, the microspectrometer merely has a fluidic interface in the form of the connecting pieces 34 and electrical connections which may be realized by plug connectors. Since all of the optical components are in a fixed spatial relationship with one another, no adjustments whatsoever are required for measurements to be carried out.

Figure 7:
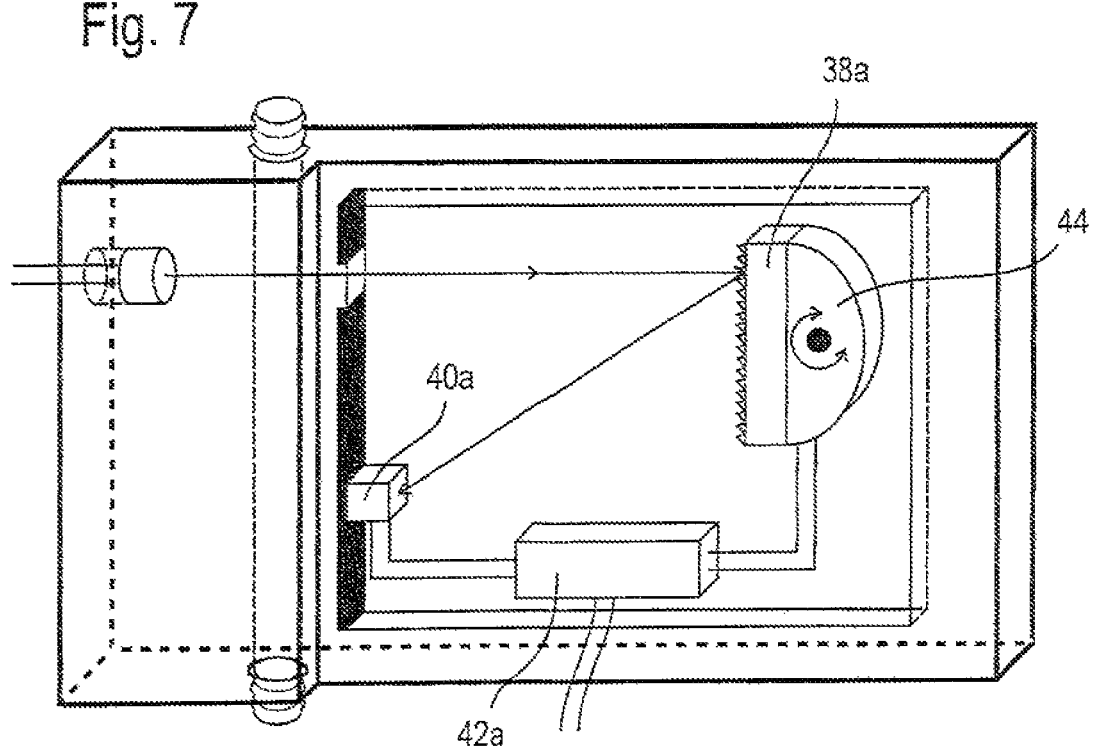
FIG. 7 shows a further embodiment using the housing according to FIG. 5.

The embodiment of FIG. 7 differs from that according to FIG. 6 in that use is made of a rotatably arranged diffraction grating 38a with a rotary drive 44 and that one single photodiode 40a is used as the detector. The rotary drive 44 is driven by the electronic evaluation unit 42a in such a manner that the photodiode 40a successively detects all spectral components of the light reflected by the grating.

Figure 8:
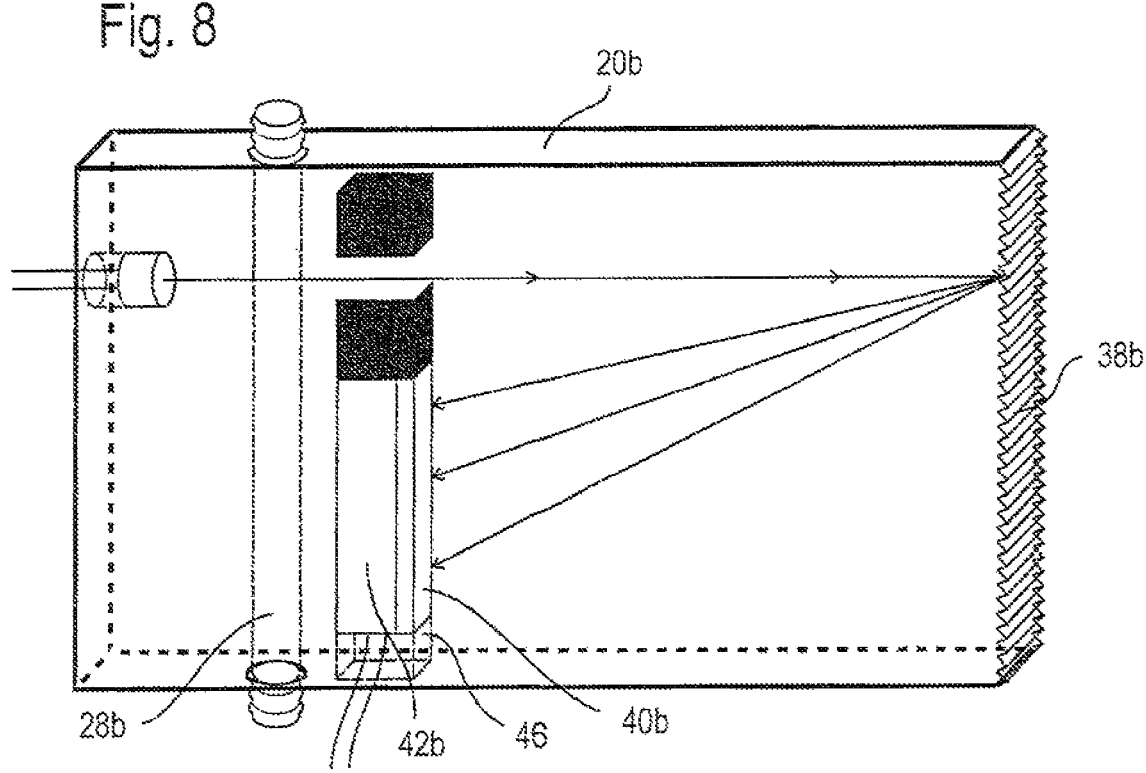
FIG. 8 shows a further embodiment using a rigid molded body as the housing.

In the embodiment according to FIG. 8, the molded body 20b forms a unitary flat cuboid made of a transparent plastic material. A recess 46 that is applied in the molded body 20b parallel to the duct 28b accommodates the photodetector row 40b and the electronic evaluation unit 42b. The diffraction grating 38b is molded into the outer surface of the molded body 20b opposite the light source 32b and is provided with a reflective coating, which is applied by vapor deposition, for example. Further, the grating 38b is expediently provided with a protective layer.

The invention claimed is:

1. A microspectrometer for fluid media comprising:
   a housing including a molded body having an outer surface, the housing containing: a fluid channel, a light source for directing light towards the fluid channel, a reflective diffraction grating, a detector, and an optoelectric evaluation unit,
   an optical measuring path of the directed light starting from the light source, passing through the fluid channel, and impinging on the diffraction grating, wherein light components of the directed light reflected by the diffraction grating impinge on the detector, and wherein a part of the outer surface of the molded body forms the reflective diffraction grating,
   wherein the housing further includes a recess extending parallel to the fluid channel for receiving the optoelectric evaluation unit, the recess being positioned between the fluid channel and the diffraction grating and extending in a direction that intersects the optical measuring path.

2. The microspectrometer according to claim 1, wherein an adjustable optical diaphragm is arranged on the optical measuring path between the fluid channel and the diffraction grating.

3. The microspectrometer according to claim 1, comprising a mirror which is firmly arranged in the housing and faces the diffraction grating, which is configured as a reflection grating.

4. The microspectrometer according to claim 3, wherein the mirror is attached to an optical diaphragm arranged on the optical measuring path between the fluid channel and the diffraction grating.

5. The microspectrometer according to claim 4, wherein the mirror extends parallel to the optical diaphragm.

6. The microspectrometer according to claim 1, wherein the housing is produced using an injection molding technology.

7. The microspectrometer according to claim 6, wherein the fluid channel is defined by a transparent wall, at least in the region of the optical measuring path.

8. The microspectrometer according to claim 6, wherein the fluid channel is formed by a tube section inserted in the housing and made from a transparent material at least in the region of the optical measuring path.

9. The microspectrometer according to claim 1, wherein the fluid channel includes ports for insertion into a conduit.

10. The microspectrometer according to claim 1, wherein a plurality of light sources having different light spectra is firmly arranged in the housing.

11. The microspectrometer according to claim 1, wherein a separate light source for scattered light measurement irradiates into the fluid channel transversely to the optical measuring path and the scattered light exiting transversely to the fluid channel impinges on the diffraction grating.

12. The microspectrometer according to claim 1, wherein scattered light from the light source exiting from the fluid channel transversely to the optical measuring path is received by a separate light receiver for scattered light measurement without a spectral dispersion.

13. The microspectrometer according to claim 12, wherein light traveling along the optical measuring path is reflected by the diffraction grating and the scattered light traveling transversely to the optical measuring path passes to the separate light receiver without being reflected by the diffraction grating.

14. The microspectrometer according to claim 1, wherein the housing has recesses for receiving optical components and the fluid channel is guided starting from one side of the molded body, passing through it up to the opposite side.

15. The microspectrometer according to claim 1, wherein scattered light from the light source that exits from the fluid channel transversely to the optical measuring path is received by a separate light receiver for scattered light measurement without passing to the diffracting grating.

16. The microspectrometer according to claim 1, wherein the outer surface of the molded body is provided with a reflective coating to form the reflective diffraction grating.

17. A microspectrometer for fluid media comprising:
   a housing including a molded body having an outer surface, the housing containing: a fluid channel, a light source for directing light towards the fluid channel, a reflective diffraction grating, and a detector;
   an optical measuring path of the directed light starting from the light source, passing through the fluid channel, and impinging on the diffraction grating, wherein light components of the directed light reflected by the diffraction grating impinge on the detector, and wherein a part of the outer surface of the molded body forms the reflective diffraction grating, optical diaphragm being arranged on the optical measuring path between the fluid channel and the diffraction grating and having an adjustable diameter.

* * * * *